(12) United States Patent
Wickham

(10) Patent No.: US 10,709,848 B2
(45) Date of Patent: *Jul. 14, 2020

(54) SEGMENTED SAFETY COVER FOR NEEDLE DELIVERY

(71) Applicant: Henry Wickham, Auckland (NZ)

(72) Inventor: Henry Wickham, Auckland (NZ)

(*) Notice: Subject to any disclaimer, the term of this patent is extended or adjusted under 35 U.S.C. 154(b) by 469 days.

This patent is subject to a terminal disclaimer.

(21) Appl. No.: 15/432,816

(22) Filed: Feb. 14, 2017

(65) Prior Publication Data

US 2017/0281878 A1 Oct. 5, 2017

Related U.S. Application Data

(63) Continuation-in-part of application No. 15/089,390, filed on Apr. 1, 2016, now Pat. No. 9,662,455.

(51) Int. Cl.
*A61M 5/32* (2006.01)
*A61B 10/02* (2006.01)
*A61B 5/15* (2006.01)
*A61B 5/153* (2006.01)

(52) U.S. Cl.
CPC ........ *A61M 5/3245* (2013.01); *A61B 5/15003* (2013.01); *A61B 5/153* (2013.01); *A61B 5/150389* (2013.01); *A61B 5/150519* (2013.01); *A61B 5/150656* (2013.01); *A61B 5/150839* (2013.01); *A61B 10/02* (2013.01); *A61B 10/0233* (2013.01); *A61M 5/3204* (2013.01); *A61M 5/326* (2013.01); *A61M 5/3216* (2013.01)

(58) Field of Classification Search
CPC ........ A61M 5/3216; A61M 2005/3267; A61M 5/3219; Y10S 128/919; A61B 5/150633
See application file for complete search history.

(56) References Cited

U.S. PATENT DOCUMENTS 6,280,420 B1 * 8/2001 Ferguson ............ A61M 5/3275
604/192
2002/0165498 A1 * 11/2002 Ward, Jr. ............ A61M 5/3202
604/198

* cited by examiner

*Primary Examiner* — Emily L Schmidt
(74) *Attorney, Agent, or Firm* — Mark A. Litman & Assoc. P.A.

(57) ABSTRACT

A segmented safety cover may include a proximal segment combined with a needle hub; a needle cannula that extends from the proximal needle hub to a distal sharpened end; a distal end cap with a hollow bore through which the needle cannula passes; a centrally mounted toggle locking mechanism, separating the proximal needle hub from the distal end cap; the toggle locking mechanism is torsion spring assisted; a proximal cover segment is connected to the hub via a proximal hinge and a distal cover segment is connected to the end cap via a distal hinge; said proximal cover segment and said distal cover segment of said toggle locking mechanism being configured with abutting faces when the segmented safety cover is in a safety mode; and wherein the proximal hinge, abutting faces and distal hinge are in line in the safe mode.

17 Claims, 8 Drawing Sheets

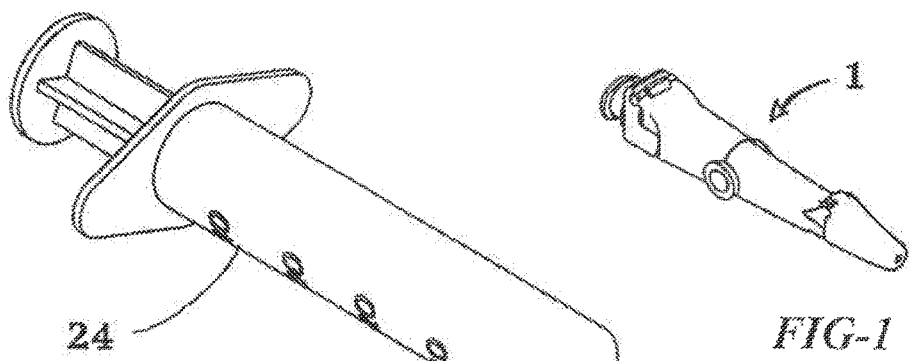
FIG-1
FIG-2
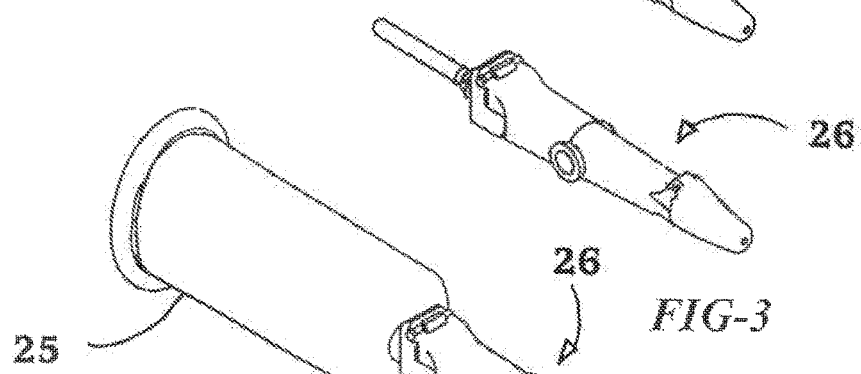
FIG-3
FIG-4
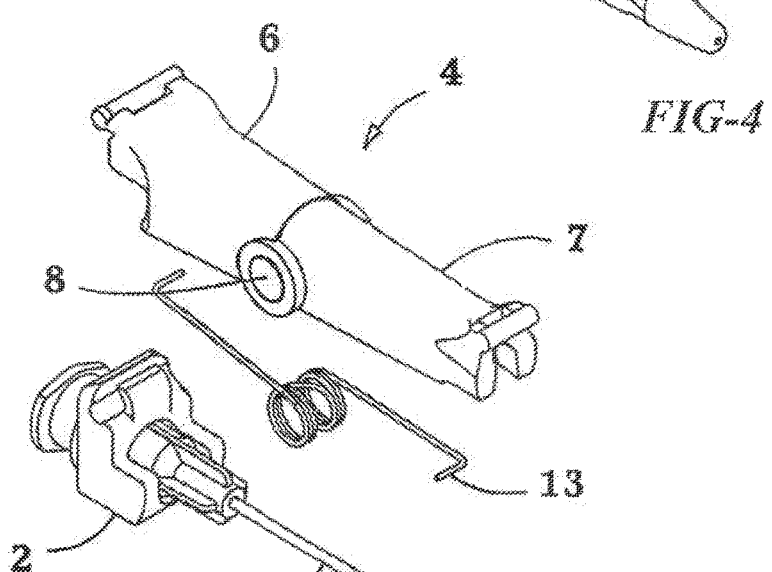
FIG-5

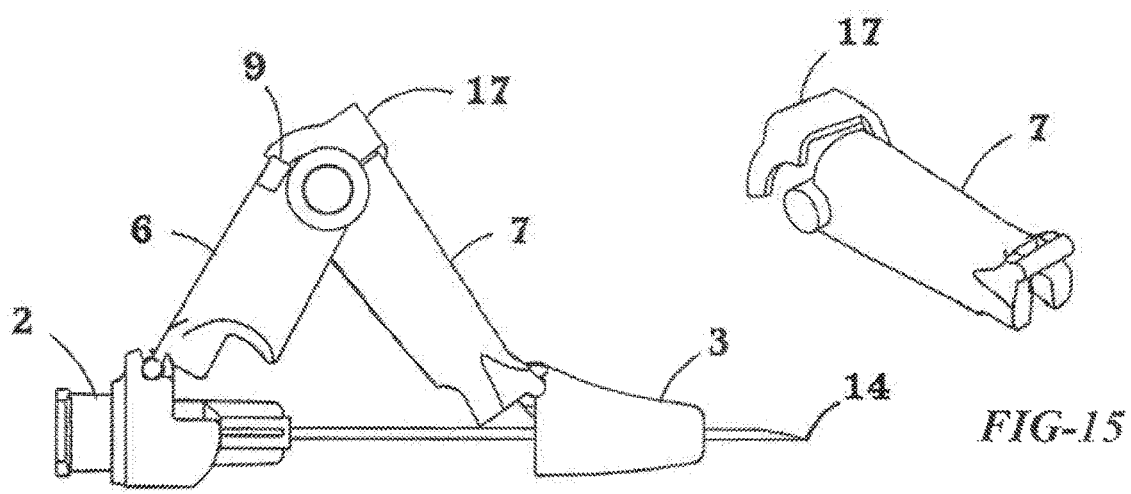
FIG-15  FIG-16
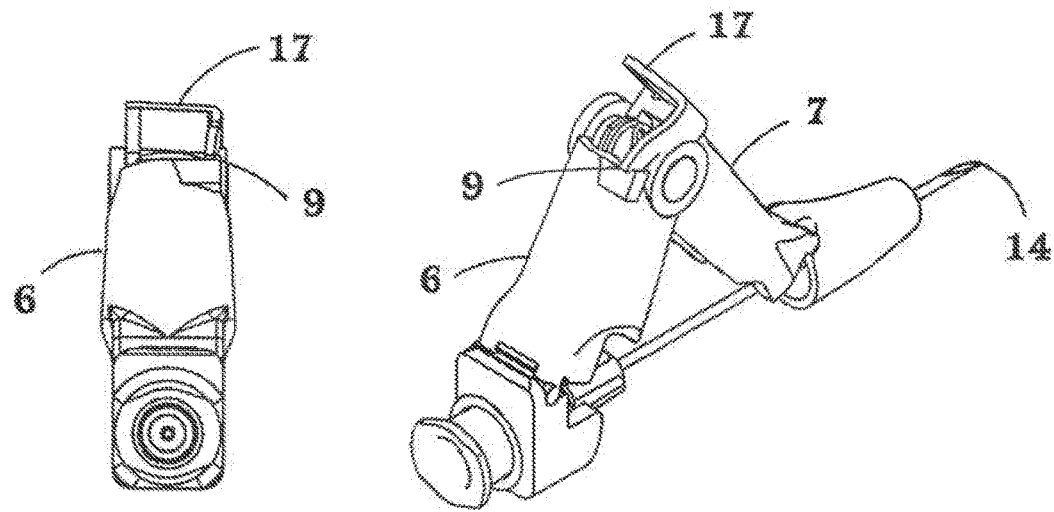
FIG-17  FIG-18
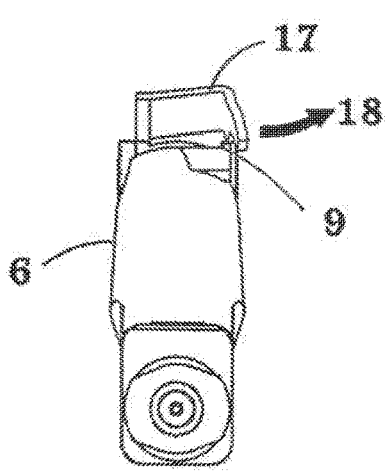 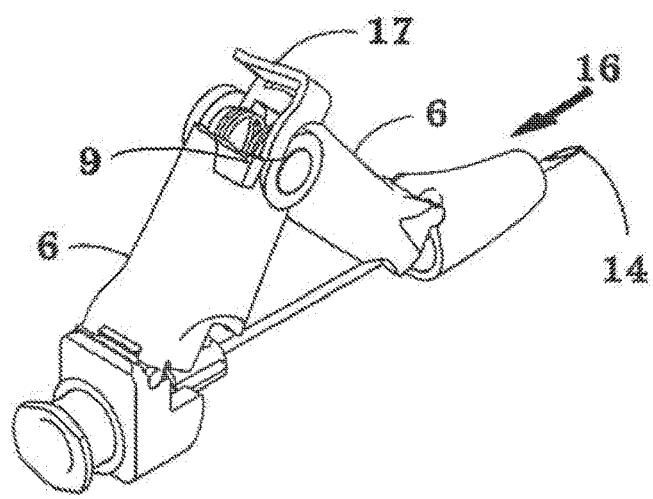
FIG-19  FIG-20

SEGMENTED SAFETY COVER FOR NEEDLE DELIVERY

RELATED APPLICATION DATA

This application claims priority under 35 USC 120 as a Continuation-in-Part of copending U.S. patent application Ser. No. 15/089,390, filed 1 Apr. 2016 and titled "SEGMENTED SAFETY COVER FOR NEEDLE DELIVERY."

BACKGROUND OF THE INVENTION

1. Field of the Invention

This invention relates to safety guards to protect against needle stick injuries used in medical and veterinary medical use of material delivery and material removal needles.

2. Background of the Art

According to the Occupational Safety and Health Administration (OSHA), needle stick injuries occur during all aspects of handling. 50% of incidents occur during the invasive procedure (while introducing needle, by accidental needle withdrawal during procedure, or during needle withdrawal at the end of the procedure).

Ironically, the vast majority of safety needle devices currently on the market only give protection to the healthcare worker after completion of the invasive procedure.

Examples of disclosures of safety devices which protect needles by moving a protective shield over the sharp end of the needle are bountiful. Most of the disclosures describe a technique where the needle tip is exposed by first removing a protective cap and where the protective shield is moved form a collapsed position proximal to the user to a distal and extended position to cover the needle tip only after the invasive procedure has been completed.

U.S. Pat. No. 6,280,420 (Ferguson) describes an active (user activated) retractable and extendable medical needle protective shield which provides opportunity for accessing and re-accessing a medical needle and associated sharpened needle tip and recovering the needle and tip for safety between accesses.

A method for infusing fluids to a subject is disclosed—A needle cover is first removed to reveal an unbiased segmented shield in the folded back state which fully exposes the needle. The segmented shield is manually extended over the needle canula and tip after use. A releasable latch is described which can be unlatched to permit refolding of shield and allow re-access to said needle and sharpened tip Once extended, the segmented shield completely covers the tip of the needle and it relies on an un-releasable latch/catch to permanently lock it into its extended position after use. One limitation of this device is that it doesn't give any protection until manually engaged and manually locked by fully extending it over the needle tip US Patent 2002/0165498 (Ward) discloses a passively (automatically) activated needle assembly, a shield assembly and a safety cap. The needle assembly includes a hub and a needle cannula that projects from the hub. The shield assembly includes a safety shield that is mounting for sliding movement along the needle cannula. The shield assembly also includes a plurality of arms articulated to one another to permit sliding movement of the safety shield along the needle cannula from a proximal position to a distal position where the tip of the needle cannula is shielded. A spring is mounted to the shield assembly and is operative to drive the safety shield from its proximal to its distal position. A safety cap is mounted over the shield assembly and holds it in the proximal position. The arms are held during usage of the safety needle. The device is not secure when extended and has to rely on an irreversible biasing clip (item 40) to physically block the path of the needle when fully extended.

The limitations of this device are that it requires the user to hold the arms back during procedure and if unintended activation does occur, the syringe would have to be discarded prior to the infusion procedure U.S. Pat. No. 7,361,159 (Fisher) describes a passive (automatically activating) safety apparatus which includes a needle hub having an arm extending therefrom and an extensible frame connected to the needle hub. The extensible frame includes a proximal segment that is hingedly connected to a distal segment. The extensible frame is resiliently biased from a retracted position to an extended position, wherein the arm releasably engages the proximal segment to fix the extensible frame in a position between the retracted position and the extended position. In an alternate embodiment, the safety apparatus includes an extensible frame including a proximal segment which is hingedly connected to a distal segment. A resilient member is coupled to the proximal segment and the distal segment. The resilient member is configured to bias the extensible frame from a retracted position to an extended position. A method for infusing fluids to a subject is disclosed.

The extendable frame is constrained in a position between the retracted and extended. To activate, a separate sheath cap is first removed to expose the needle cannula. The extendable frame extends a needle cover over the needle cannula tip and the device relies on an irreversible biasing clip to physically block the path of the needle when fully extended. Different removable sheath configurations are utilized to prevent the automatic locking cover from actuating when liquid is drawn from a vial in preparation for the infusion procedure.

The limitations of this device are that it relies on removable sheaths to prevent automatic locking and if unintended activation does occur the syringe would have to be discarded prior to the infusion procedure Although Ferguson describes a device of which the needle can be re-acessed, these features have to be activated intentionally and manually. Simply adding a spring to this device is not an option as the locking features present in this device are latched in place and has to be manually de-latched for re-access. All the relevant disclosures including Ferguson, Ward and Fisher describe a device where a needle cover first has to be removed thereby exposing the needle tip rendering it unprotected.

U.S. Pat. No. 5,634,909 (Schmitz) discloses a hypodermic injection system utilizes disposable medicament ampules having self-contained needles operated by a re-useable actuator to extend the needle from complete enclosure within the ampule out and into the flesh and inject the medicament as it moves, the needle automatically retracting into the disposable ampule after exhausting its contents, completely eliminating any need to handle the exposed needle before or after use.

U.S. Pat. Nos. 5,188,599 and 4,994,034 (Botich) disclose a hypodermic injection system (7) with a retractable needle (9) wherein the needle (9) retracts within an interior cavity (71) of a syringe plunger (59), such that the needle (9) is confinedly held within the plunger (59). A cylindrical spring housing (21) has resilient fingers (23) which captures a spring (15) biasly holding a needle holder (11) against the retaining force of resilient fingers (23). The plunger (59) has a frangible end (65), which dissociates when the outwardly tapered shoulders (68) spread the resilient fingers (23), allowing the coiled spring (15) to eject the needle (9) and its holder (11) into the interior cavity (71) of the syringe plunger (59). A body fluid sampling embodiment employs the same functional elements except the plunger (59") is shorter and contains a linking needle (137) that communicates with a vacuum container (147). The container allows fluid sampling and provides the structure to release the spring (15") retracting the needle (9").

U.S. Pat. No. 4,955,866 (Corey) provides a recapping device for use with medical devices including all hollow and solid medical needles of the type used for entry into the body and into closed intravenous and intraarterial systems for access, sampling, and injection of medications, and are withdrawn after use. The recapping device includes a hollow sleeve encircling a portion of the needle and having a distal end aperture adapted to permit the sleeve to slide between a first position on the medical device wherein the needle is exposed to enable use of the needle, and a second position characterized by the distal end of the needle being contained within the distal end capped hollow sleeve, and the device may optionally contain a housing for a free-floating fenestrated disk, which, upon movement of the device to its second position wherein the tip of the needle exits the distal end aperture, shifts position to provide an obstruction at that aperture. A securing means for the hollow sleeve, such as a tether, is provided for permitting substantially free slidable movement of the hollow sleeve between the first and second positions.

US Published Patent Application Nos. 20080132838 20100100039 20110226646 (Wyrick) disclose a reloadable medicine injector and methods are described in which a barrel with a receiving cavity is adapted to slidably receive a syringe subassembly for axial movement therein. Upon removal of a safety and release of a syringe driver, the syringe driver moves forward and injects the syringe needle. A plurality of penetration controls are shown for controlling injection needle penetration depth. The penetration controls have an abutment and various lengths to provide different needle penetration depth positions. In one form of penetration control a sleeve is used against which the syringe or related parts contact. In another form the front return spring is used as a penetration control. A cushioning ring may be used to reduce syringe breakage. A load distribution and guide ring may be used to distribute loading applied to the syringe and help guide the moving syringe.

US Published Patent Application No. 20070078409 (Salyz) escribes a protective needle guard assembly features a hub that is removably secured to a reusable syringes, a first and a second needle extending outwardly from the hub in opposite directions, and a moveable sheath that moves about an outer surface of the syringe. The needle guard includes an engagement device that engages the moveable sheath to secure the moveable sheath in an extended position wherein the moveable sheath extends beyond the distal end of the first needle. The moveable sheath features a retracted position wherein the first needle is substantially exposed. A cavity formed in the hub substantially covers and protects the second needle.

Other relevant disclosures are included in U.S. Pat. Nos. 5,348,544; 5,910,130; 5,256,152; 4,935,013; 4,735,618; 5,250,031; 5,295,972; and 5,584,818; and US20110066107; and EP0 654281.

Apart from Ferguson, most of the disclosures describe a way of blocking the needle path by means of a metallic clip or rotating member located in the distal needle cap and this only after the invasive procedure has been completed. The limitations of this approach means that the medical device has to be discarded if unintentionally activated. As can be seen, these disclosures still are not believed to offers high levels of security and additional advances are still needed. These disclosures are incorporated herein by reference in their entirety by reference.

SUMMARY OF THE INVENTION

A segmented safety cover may include:
a) a proximal segment combined with a needle hub;
b) a needle cannula that extends from the proximal needle hub to a distal sharpened end.
c) a distal end cap with a hollow bore through which the cannula shaft passes
d) A centrally mounted toggle locking mechanism, separating the proximal needle hub from the distal end cap, hingedly connected to both and maintaining the needle guard in a position where it completely covers the needle tip
e) wherein the toggle locking mechanism is torsion spring assisted and consist of proximal and distal cover segments which overlays the cannula shaft and is linked together through a central hinge
f) wherein the proximal cover segment is connected to the hub via a proximal hinge and the distal cover segment is connected to the end cap via a distal hinge
g) said proximal cover segment and said distal cover segment of said toggle locking mechanism being configured with abutting faces that contact each other above said central hinge when the segmented safety cover is in a safety mode; and
h) wherein the proximal hinge, abutting faces and distal hinge are in line in the safe mode so that a force exerted on the distal end cap is translated directly onto the abutting faces above the central hinge thereby maintaining the device in its secured state.

The abutting faces each have one flat face, and the two flat faces form a plane at the intersection of the two flat faces with each face having a top portion on the flat face and a bottom portion on the flat face. When a linear force is applied parallel to the plane of the abutting two faces it will result in the central hinge to be elevated, the two flat faces are forced to separate, with the two top portions of the faces initially being separated from each other at a faster rate than that at which the two bottom portions separate under the influence of the linear force. This linear force may also be considered as a vector force passing near the two abutting faces from below the plane of all contact points between the two abutting faces. The proximal hinge, distal hinge and central hinge are configured to form a triangle configuration when the segmented safety cover is in a delivery mode for a needle with the distal cover segment and the distal end cap slide with respect to the needle cannula. The proximal cover segment appears to rotate relative to the hub, and the distal cover segment appears to rotate relative to the sliding distal end cap as it slides horizontally with respect to the needle cannula.

BRIEF DESCRIPTION OF THE FIGURES

FIG. 1 is an isometric view of the device
FIG. 2 is an isometric view of the device mounted on a syringe
FIG. 3 is an isometric view of the device configured as a phlebotomy needle.

FIG. 4 is an isometric view of the phlebotomy configuration mounted on its holder FIG. 5 is an exploded view of the device.

FIG. 15 is an isometric view of the distal cover segment with the resiliently biased or spring loaded wedge extension.

FIG. 16 is a side view of the device in its temporary dislocated position with the resiliently biased wedge pushed up against the abutting face of the distal cover segment.

FIG. 17 is a rear view of the device in its temporary dislocated position with the resiliently biased wedge pushed up against the abutting face FIG. 18 is an isometric view of the device in its temporary dislocated position with the resiliently biased wedge pushed up against the abutting face FIG. 19 is a rear view of the device shown with the resiliently biased wedge dislocated by a digital force applied to the distal end cap.

FIG. 20 is an isometric view of the device shown with the resiliently biased wedge dislocated by a digital force applied to the distal end cap.

DETAILED DESCRIPTION OF THE INVENTION

Figure 6:
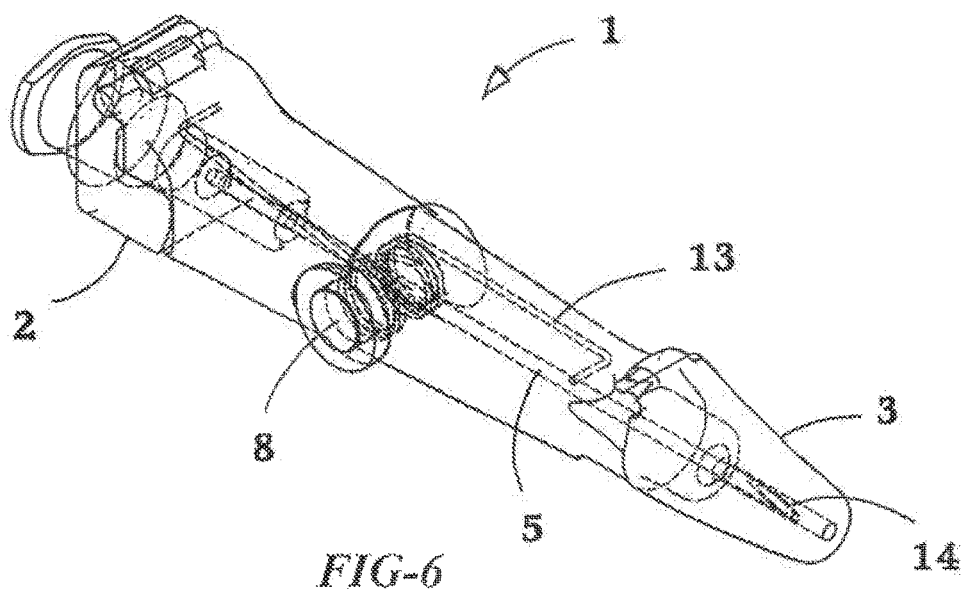
FIG. 6 is an isometric view of the device with hidden detail.

This invention addresses shortcomings by enabling a device that renders the medical needle (e.g., injection, biopsy, sampling, and sensor needles) safe at all times. This invention device has the needle tip exposed by manual intervention just prior to being inserted into the patient. It then passively returns to its secured position while the needle is withdrawn from the patient.

This device of the invention has a hinged cover arrangement that is in its extended position prior to being used and where a protective cap and protective shield is integrated and thus not removed to offer protection at all times. The needle tip is exposed just prior to the invasive procedure. It then automatically secures itself again as the needle is removed from the patient.

A segmented safety cover may include:
a) a proximal segment combined with a needle hub. The hub is a structural element that may abut, secures or connects the proximal segment to another component such as a support or medical delivery or removal system (e.g., syringes, vacuum pressure, sampling pressure, sensing electronics, etc.);
b) a needle cannula that is mounted in the needle hub and extends from the hub to a distal sharpened end
c) a distal end cap with a hollow bore through which a cannula shaft passes. The segments and other components are made of substantive structural material that will not bend or distort under common forces encountered during normal use. The various segments of the cover may comprise polymeric materials (thermoplastic or thermoset), metallic materials, ceramics, composites or the like. Transparent, opaque or translucent materials may be used;
d) an engaged, torsion spring assisted, centrally hinged toggle locking mechanism that overlays the cannula shaft; The spring must be a resilient material, such as metals, or polymers that do not elastically deform during the full motion of the segments.
e) wherein the toggle locking mechanism consist of a proximal and distal cover segments linked together through a central hinge.
f) The central hinge is also preferably a full construction that allows rotation of one side (top or bottom) of the distal and proximal cover segments, such as the abutting sides.
g) said proximal cover segment and said distal cover segment are configured with abutting faces that contact each other above (not necessarily along the entire abutting faces, but at least the tops of those faces) said central hinge when the segmented safety cover is in a safety mode;
h) said proximal cover segment is hingedly connected to said proximal needle hub and said distal cover segment is hingedly connected to said distal end cap
i) wherein the proximal hinge, abutting faces and distal hinge are in line and the central hinge below the abutting faces so that any force exerted on the distal end cap would be translated directly onto the abutting faces thereby maintaining the device in its secured and safe state.

The abutting faces each have one flat face, and the two flat faces are relatively perpendicular to an access port or cannula in the segmented cover. Each of the flat faces is rotationally engaged with the central hinge and from an abutting position, the two flat faces are configured to rotate away from each other. The two flat faces, in the safe configuration of the segmented cover form a plane at the intersection of the two flat faces with each face having a top portion on the flat face in contact with the other flat face and a bottom portion on the flat face in contact with the other flat surface. When a linear force is applied parallel to the plane of the abutting two faces and a vector of the force passes near the two abutting faces from below the plane of the two abutting faces, the two flat faces are forced to separate as the central hinge is elevated, with the two top portions of the faces initially being separated (from the abutting safe configuration) from each other at a faster rate than that at which the two bottom portions separate (from the safe configuration) under the influence of the linear force. The application of the force, without movement of any other elements of the segmented cover (the stabilization of ends of the segmented cover to allow motivating action of the force is not movement of an element of the segmented cover). This can be referred to as dislocating force applied parallel to the abutting faces, as it causes separation or dislocation of the abutting faces from each other. The proximal, distal and central hinge are configured to form a triangle configuration when the segmented safety cover is in a delivery mode for a needle with the distal cover segment rotated in a clockwise direction away from the proximal cover segment and the distal cover segment appears to rotate clockwise towards and with respect to the distal end cap as the distal end cap slides horizontally with respect to the needle cannula.

The segmented safety cover will have a needle present in the needle hub and an injection end of the needle is within the distal end cap during a medical procedure. Upon forming the triangular configuration, the distal end cap is configured to retract over the needle and towards the needle hub, the distal segment appears to rotate with respect to the distal end cap as the distal end cap retracts and exposes the injection end of the needle. In the safety mode, the distal segment and proximal segment are in a secured mode, resisting movement of the distal segment and the proximal segment by the torsion spring.

Two manually operated pressure plates overlap sides of the distal cover segment and the proximal cover segment and the plates are configured to temporary dislocate the secured and safe mode when pressure is applied to the two pressure plates.

The pressure plates are resiliently biased to disengage from the dislocated mode to return to a secured ready mode when triggered by said distal end cap as it pushes against a patient's skin during the injection procedure. This frees the device to return to its initial SECURED AND SAFE mode as the needle is withdrawn from the patient.

The torsion spring may be a single or preferably a double coil spring with a first extension of the double coil spring extending approximately parallel to the distal cover segment in the safety mode, and a second extension of the double coil spring extending approximately parallel to the proximal cover segment in the safety mode. The first one coil of the double coil spring may be on a first side of the cannula shaft and a second one coil of the double coil spring may be on a second and opposite side of the cannula shaft with respect to the first coil.

The segmented safety cover will have a needle present within the cover, and the segmented safety cover is configured so that the pointed injection end of the needle is completely covered by the distal end cap when the torsion spring is secured in the safety mode, and the pointed injection end of the needle is exposed out of the distal end cap when the safety mode is removed and compressive force applied by the torsion spring retracts the distal end cap by rotation of both the proximal cover segment and the distal cover segment about the central hinge.

A method for enabling injection of fluids using the segmented safety cover with a needle present within the cover of the present technology may include applying force to both the proximal cover segment and the distal cover segment from the torsion spring to elevate the central hinge and retract the distal end cap to slide the hollow bore within the distal end cap over the needle to expose the needle.

A segmented safety cover may be alternatively described as including:
  a) A proximal segment fixed with a needle hub, said proximal segment also being integrated with a syringe body or a blood collecting needle;
  b) A distal end cap with a hollow bore that covers a cannula shaft through which said cannula shaft may pass;
  c) A rigidly interlocked, torsion spring assisted centrally hinged toggle locking mechanism that covers the cannula shaft, where said toggle locking mechanism comprises of a hollow proximal cover segment and hollow distal cover segment linked through a central hinge;
  d) Wherein said proximal cover segment and distal cover segment are configured with vertical protruding abutting faces above said central hinge;
  e) Wherein a proximal cover segment of said toggle locking mechanism is hingedly connected to said proximal hub by a proximal hinge and said distal cover segment of said toggle locking mechanism is hingedly connected to said distal end cap by a distal hinge;
  f) Wherein the proximal hinge, distal hinge and central hinge are arranged in the form of an inverted triangle formed by a line connecting said proximal and said distal hinges that lies parallel to the cannula shaft and said central hinge defining a vertex of the inverted triangle below said proximal and distal hinges.

The abutting faces rotate away from each other when a force parallel to a plane formed between the abutting faces is applied upwardly towards the abutting faces. The upward force may have a vector coincident with that plane between the abutting faces.

The torsion spring is biased to maintain the toggle locking mechanism in a secured position. The torsion spring may be centered to and fitted on an inside of said centre hinge and comprises single or double coil loops on one or either side of the needle that allows the center hinge with coil loops to be lowered past said needle cannula without interference by said cannula shaft.

The toggle locking mechanism may include a resilient wedge mechanism which is configured to be pressure activated to arrest said toggle locking mechanism in a temporary dislocated position to enable exposure of said cannula tip prior to the invasive procedure. The wedge mechanism may include a resilient wedge extension mounted on the distal cover segment or proximal cover segment, and the resilient wedge extension is located above the center hinge. The wedge may be configured to be clamped into a wedged-in position by spring force generated by the torsion spring, and the wedge is resiliently biased to dislocate from a wedged-in position when pressure applied by the torsion spring is reduced when said distal end cap pushes against a patient's skin.

The wedge may be integrated into a latch disk with single or multiple recess features on an inside face of the latch disk and a retention face on the wedge that allows it to wedge into/against a retention face on the proximal cover segment or distal cover segment when the wedge is pressure activated.

A further alternative description of the device and its operation is herein provided as follows. The segmented needle-protection cover may have at least five segments which are, in order from a point distal from the point on insertion of a needle:
  a) a hub element;
  b) a proximal first needle cannula cover segment;
  c) a central hinge;
  d) a distal second needle cannula cover segment; and
  e) a distal end cap.

The features of the present technology that may be further considered in this description may include facts wherein:
1) This device is secured and safe in rest/start position— all other devices is partly collapsed in rest with the needle exposed
2) The centre segment may be an element that is secured in place and that this secured central element is what separates the end cap from the hub and retains the end cap over and in a fixed position of protruding past the needle tip.
3) The proximal and distal members aren't arms above the needle as in the other devices but bodies that completely covers the needle shaft (cannula.
4) The way in which the members are automatically secured to form a rigid centre segment is a unique application of a (toggle locking mechanism) and is further described herein.
5) The way in which the members can be manipulated to temporarily dislocate to present the needle tip is preferably performed just prior to the injection
6) A method and apparatus is provided for arresting (by wedging an element in-between the vertical locking faces) the device with the needle exposed.
7) How the wedge escapes (when the tip touches the patents skin) is to free the device to return to its home (secured and safe) position upon release of the wedge. Looking at a horizontal axis along which a needle would lie, passing through the needle cannula (a bore, not necessarily fully inclosing the needle, but nesting the needle in contact with an open groove in the a proximal first needle cannula cover segment and the distal second needle cannula cover segment, with the bottom of the needle length uncovered below the proximal first needle cannula cover segment and the distal second needle cannula cover segment) from the hub, past the proximal first needle cannula cover segment, the central hinge and the distal second needle cannula cover segment and into the distal end cap. The hub is in hinged connection to the proximal first needle cannula cover segment, and the distal second needle cannula cover segment is in hinged connection with the distal end cap. The elements operate with respect to rotation and alignment changes adjacent the hinges as follows, with the axis of the needle cannula being considered as approximately horizontal during a needle-safe alignment along the approximate horizontal alignment of a), b), d) and e):

1) When the proximal first needle cannula cover segment and the distal second needle cannula cover segment are in the safe, approximately horizontal alignment, the central hinge holds adjacent opposing faces of proximal first needle cannula cover segment and the distal second needle cannula cover segment in an abutting, secured (anti-rotational) position;
2) Rotation with respect to the hinge of the proximal first needle cannula cover segment (in a counter-clockwise movement with respect to the central hinge) and the distal second needle cannula cover segment (in a clockwise movement with respect to the central hinge) elevates tops of each of the opposing faces and elevates the central hinge and draws together the two most respectively distal faces or ends of the proximal first needle cannula cover segment and the distal second needle cannula cover segment, which are respectively adjacent the hub element and the distal end cap. This movement also shortens the distance between the distal end cap and the hub element, retracting the distal end cap towards the hub element.
3) Retraction of the distal end cap does not apply harmful sideways stress against any needle nesting in the needle cannula as rotation between both i) the proximal first needle cannula cover segment and hub and ii) the distal end cap and the distal second needle cannula cover segment causes both the proximal first needle cannula cover segment, the central hinge and the distal second needle cannula cover segment to elevate above the needle, removing the needle from the grooves in the proximal first needle cannula cover segment and the distal second needle cannula cover segment. This may momentarily expose said needle cannula, but not the pointed tip of the needle, except as the point of the needle extends beyond a distal end of the distal end cap as intended when the device is changed from the needle-safe position to the active needle insertion position.
4) During these movement, a rotating hinge between the hub element and the proximal first needle cannula cover segment, and a separate rotating hinge between the distal second needle cannula cover segment and the distal end cap are configured to keep the needle in the approximately horizontal position, with the portion of the needle cover cannula within the distal end cap remaining in the approximately horizontal alignment as the distal end cap retracts over the needle, exposing the needle tip during the conversion of the device to the active needle position. There is some modest stress placed on the needle from the rotation of respective elements, but essentially only at the hub element and the distal end cap. However, because little or no manual or finger (digit or digital) forces are directly applied to the end cap (where torsion stress would be most likely to deflect or stress the needle cannula), there is little significant deflecting stress applied to the needle cannula by the cover device when the needle is exposed to its active position during medical procedures, including insertion.
5) Downward force on the elevated central hinge (between the proximal first needle cannula cover segment and the distal second needle cannula cover segment lowers the central hinge, reverses all rotation of segments and extends the distal end cap over the needle tip, returning the device to its original needle safe position. The needle will again nest within the grooves in the proximal first needle cannula cover segment and the distal second needle cannula cover segment. The central hinge may or may not have a groove for nesting of the needle in the safe position.

It is to be noted that the opposed adjacent faces of the proximal first needle cannula cover segment and the distal second needle cannula cover segment resist any deflection of the length of the device by downward pressure on the central hinge. This prevents any deflecting or bending stress being applied against the included needle during handling.

FIG. 1 shows a perspective view of the Passive Safety Cover (1) in its secured position.

FIG. 2 shows a perspective view of the Passive Safety Cover (1) attached to a syringe (24).

FIG. 3 shows a perspective view of an embodiment of the Passive Safety Device as a Phlebotomy Needle (26).

FIG. 4 shows a perspective view of the Phlebotomy embodiment (26) of FIG. 3 mounted to a tube holder (25).

FIG. 5 shows an isometric exploded view of the Passive Safety Cover. The Central toggle locking mechanism (4) consist of a hollow Proximal cover segment (6) linked to a hollow Distal cover segment (7) by means of a centrally mounted hinge (8). The unidirectional double torsion spring (13) urges the central toggle locking mechanism towards its secures, needle safe position. The Needle Hub (2) is hingedly connected to the proximal hinge of the central toggle locking mechanism (4). The distal end cap (3) slides over the needle cannula (5) and is also hingedly connected to the distal hinge of the centrally hinged segment.

FIG. 6 is an isometric view of the device (1) in its secured, needle-safe position with the unidirectional double torsion spring (13) in place to maintain the central toggle locking mechanism in its extended and secured position where it separates the Hub (2) from the End Cap (3) which surrounds the Needle cannula (5) and extends past the Cannula tip (14) within the distal end cap (3).

Figure 7:
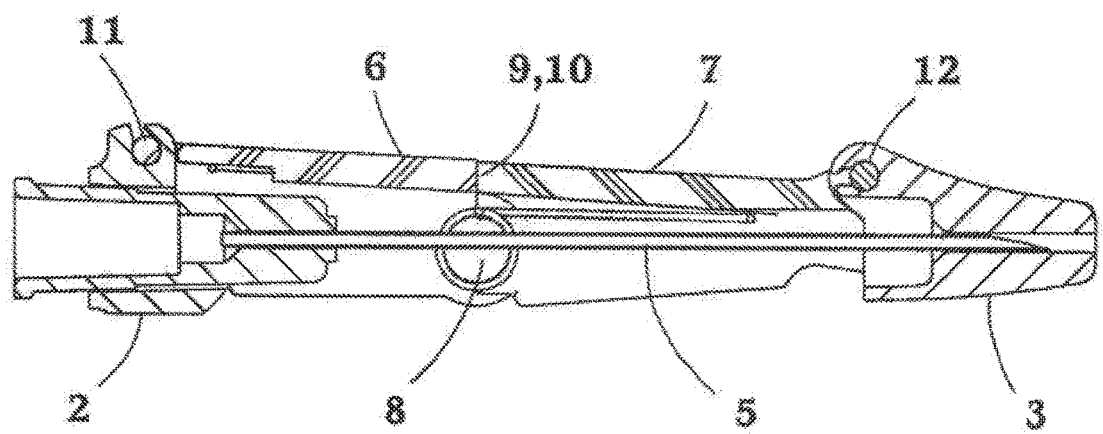
FIG. 7 is a sectioned view of the device.

FIG. 7 is a sectioned view of the device (1) in its secured, needle safe position. The vertical abutting faces, the opposed distal ends of the proximal cover segment and the opposed proximal end of the distal cover segment are shown. The vertical abutting faces (9,10) are positioned above the central hinge (8) and is pushed against each other to retain the device in its secured position. The proximal hinge (11) connects the Hub (2) to the proximal cover segment (6) of the central toggle locking mechanism of which the Distal cover segment (7) connects to the End Cap (3) via the distal hinge (12). The relatively lower position of the central hinge (8) in relation to the needle cannula (5) is also shown.

Figure 8:
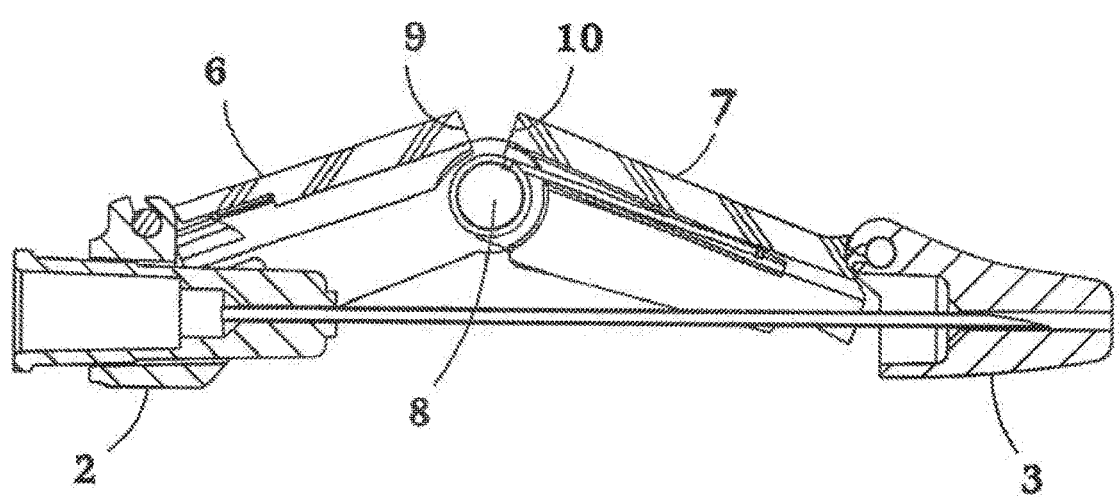
FIG. 8 is a sectioned view of the device with the central hinge of the toggle locking mechanism forced upwards to expose the abutting faces.

FIG. 8 is a sectioned view of the device in a partly dislocated position. The central hinge (8) is advanced up to a position above the needle cannula (5 in FIG. 7) The vertical abutting faces (9,10) on the proximal and distal cover segments (6,7) respectively are moving away from each other.

Figure 9:
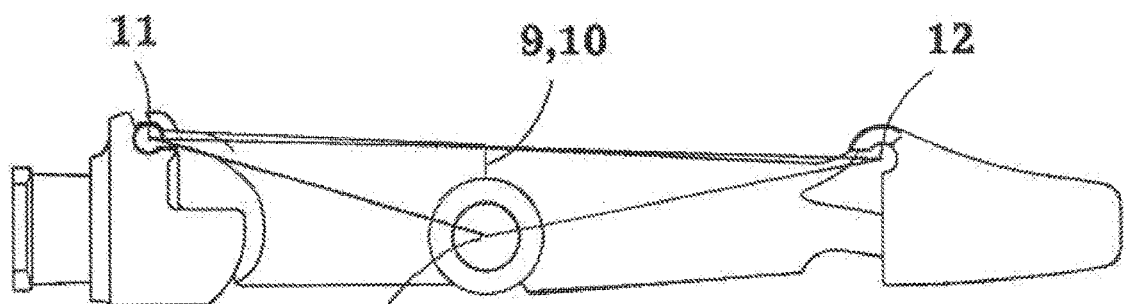
FIG. 9 is a side view of the device in its normal secured position with the central hinge below the proximal and distal hinges indicating the inverted triangular configuration.

FIG. 9 is a side view of the device in its secured position. The proximal hinge (11) and distal hinge (12) are in line and generally above the height of the central hinge (8) with the vertical abutting faces (9, 10) pushed against one another. The hinges (11 and 12) may be living hinges or pins passing through securing holes in the structural elements.

Figure 10:
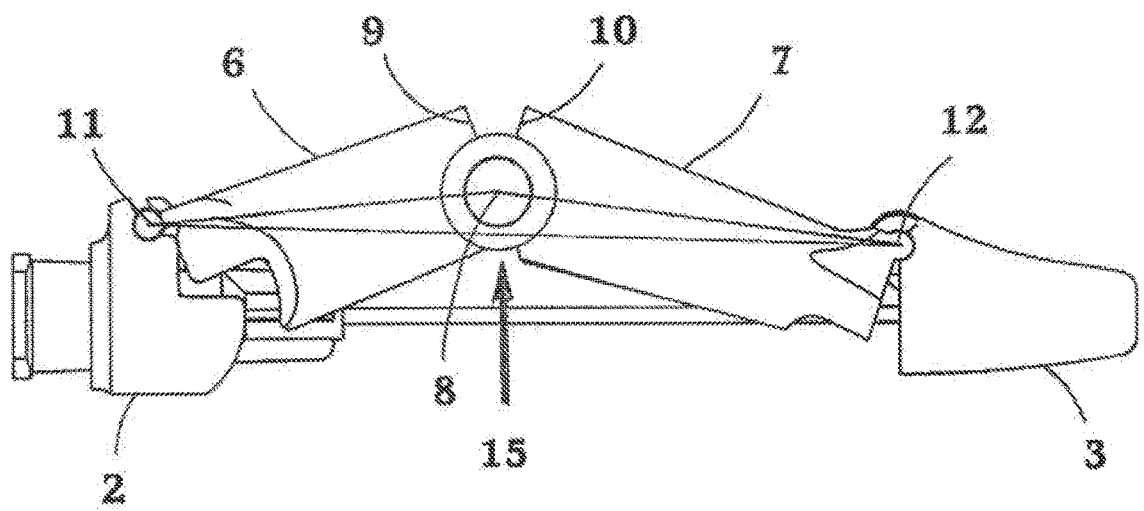
FIG. 10 is a side view of the device with the central hinge forced up to a position higher than the proximal and distal hinges indicating the upright triangular configuration.

FIG. 10 is a side view of the device with a digital (fingered) upwards force (15) applied to pull or push the central hinge (8) to a position above the cannula (5 in FIG. 5), proximal hinge (11) and distal hinge (12). The upward force (15) is an example of the dislocating force mentioned earlier. Its vector is approximately parallel to the original position/plane of the abutting faces 9, 10 in FIG. 9 and the vector is applied through the central hinge to elevate the hinge and to force apart the two abutting faces, and as shown in FIG. 10, with the top portions of the flat faces moving farther apart from each other than do the bottom portions of the faces 9, 10 after the force has dislocated or elevated the top portions of the abutting faces by rotation around the center hinge. As the hinge rotates from the dislocation force 15, the flat abutting faces separate more rapidly at the top of the flat faces than do the bottom portions because of a larger radius for movement of the top portions as compared to the bottom portions of the two faces. The proximal cover segment's (6) vertical abutting face (9) is parting from the vertical abutting face (10) of the distal cover segment (7) as the centrally hinged section dislocates and elevates.

Figure 11:
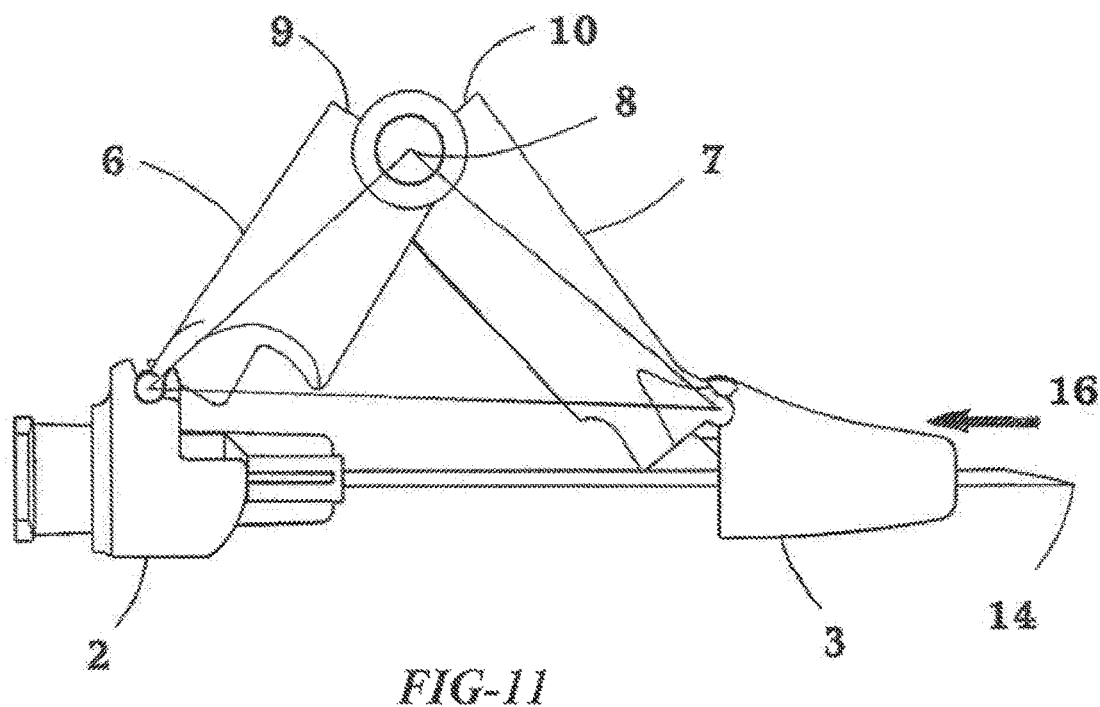
FIG. 11 is a side view of the device in its temporarily dislocated position which shows a digital force being applied to the distal end to expose the needle tip.

FIG. 11 is a side view of the device in its dislocated position where a digital (fingered) axial force (16) causes the toggle locking mechanism to collapse towards the hub (2) or the end cap (3) to retract, thereby exposing the cannula tip (14)

Figure 12:
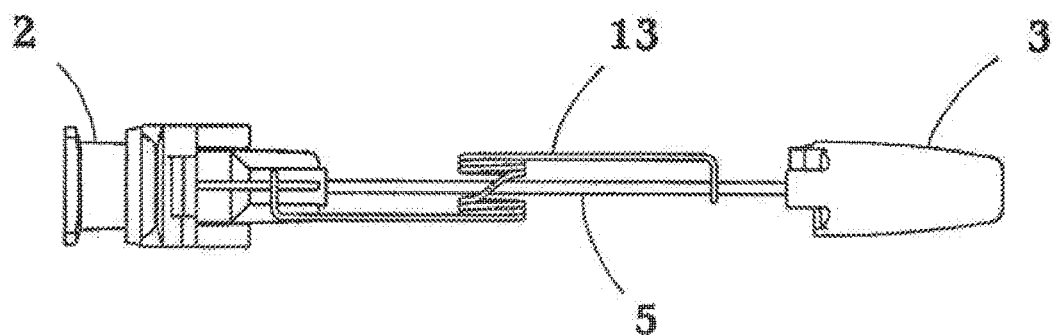
FIG. 12 is a top view with the toggle locking mechanism removed, showing the position of the unidirectional double torsion spring with its coil loops on either side of the needle cannula.

FIG. 12 is a open top view of the device with the central toggle locking mechanism removed to show the position of the unidirectional double torsion spring (13) with its with its coil loops on either side of the needle cannula (5).

Figure 13:
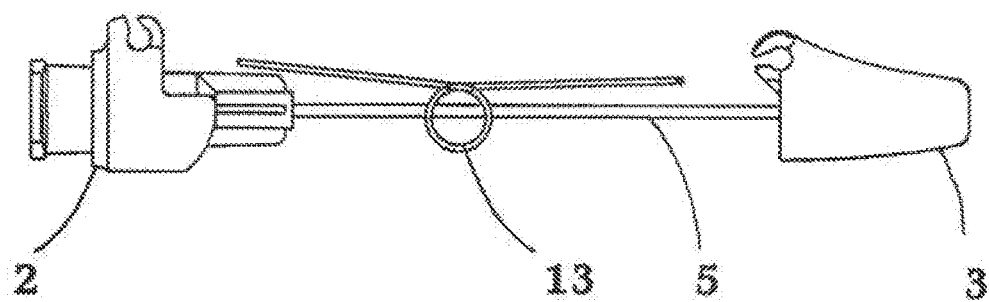
FIG. 13 is a side view showing the spring coils over the cannula center.

FIG. 13 is a side view of the device with the toggle locking mechanism removed to show the position of the unidirectional double torsion spring (13) in relation to the needle cannula (5).

Figure 14:
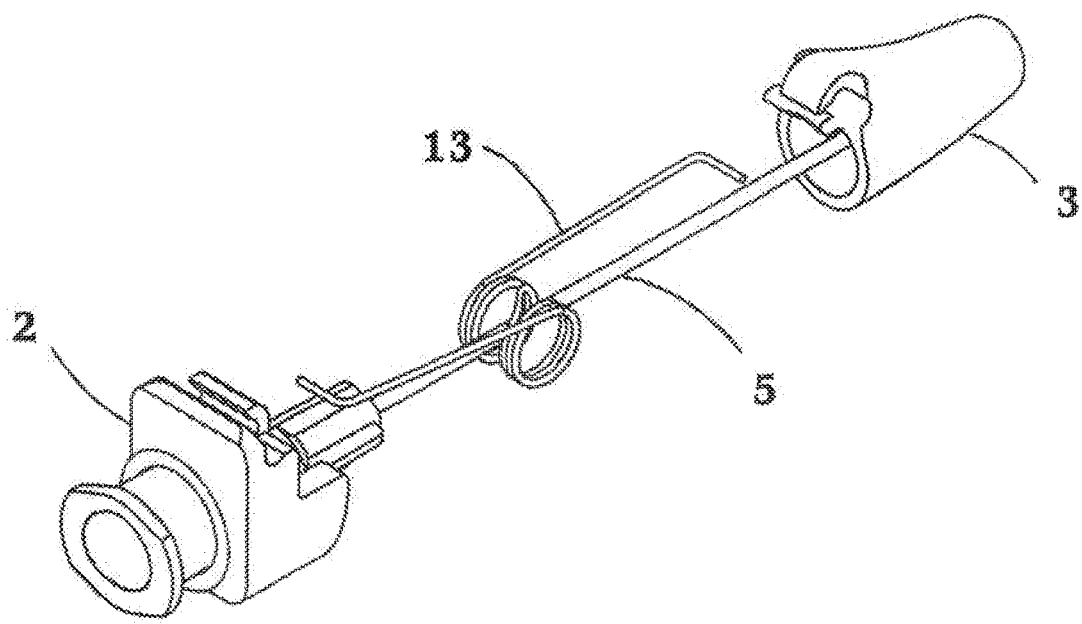
FIG. 14 is an isometric view of the spring position relative to the needle canulla.

FIG. 14 is a isometric view of the device with the central toggle locking mechanism removed to show the position of the unidirectional double torsion spring (13) between the Hub (2) and distal End Cap (3) and over the needle cannula (5).

FIG. 15 shows an angular configuration of the distal cover segment (7) of the toggle locking mechanism with a resilient wedge extension (17).

FIG. 16 shows a side view of the device in a dislocated and arrested needle (14) delivery position. The resilient wedge extension (17) is engaged and wedges against the vertical abutting face (9) of the proximal cover segment (6) of the central toggle locking mechanism. In this position, the end cap (3) has moved towards the hub (2) thereby exposing the needle tip (14).

FIG. 17 is a rear view of the device in the dislocated and arrested delivery position. The resilient wedge extension (17) is shown under tension after being forced in position by an external digital force and pushing up against the vertical abutting face (9) of the proximal cover segment (6), exposing the needle tip.

FIG. 18 is an isometric view again showing the device in its dislocated and arrested delivery position. The unidirectional double torsion spring (not shown, but see 13 in FIGS. 13 and 14) force urges the central toggle locking mechanism to extend, thus clamping and retaining the resilient wedge extension (17) in this position.

FIG. 19 is a rear view of the device with the resiliently biased wedge escaping (18) at the introduction of the external digital force (16).

FIG. 20 is an isometric view of the device and shows a digital, axial force (16) being exerted onto the end cap (3) in FIG. 16). This would take place as the patient's skin pushes onto the end cap (3). This action relieves the pressure between the vertical abutting face (9) and resiliently biased wedge (17) and causes the resiliently biased wedge (17) to move as its tension is released.

Figure 21:
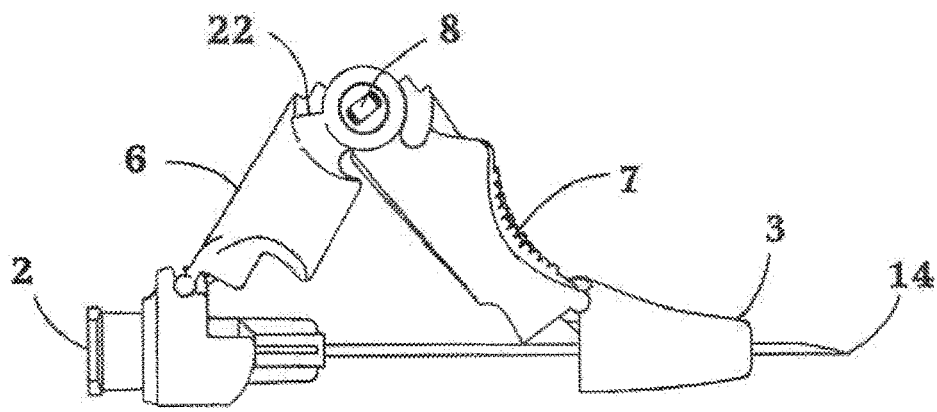
FIG. 21 is a side view of the device with the latch disk hidden to show the exposed abutting faces.

FIG. 21 is an embodiment of this device in its arrested delivery position where the wedge is integrated into a latch disk (not shown) and the abutting face is extended (22) to the side of the proximal cover segment (6). The latch disk is hidden for clarity.

Figure 22:
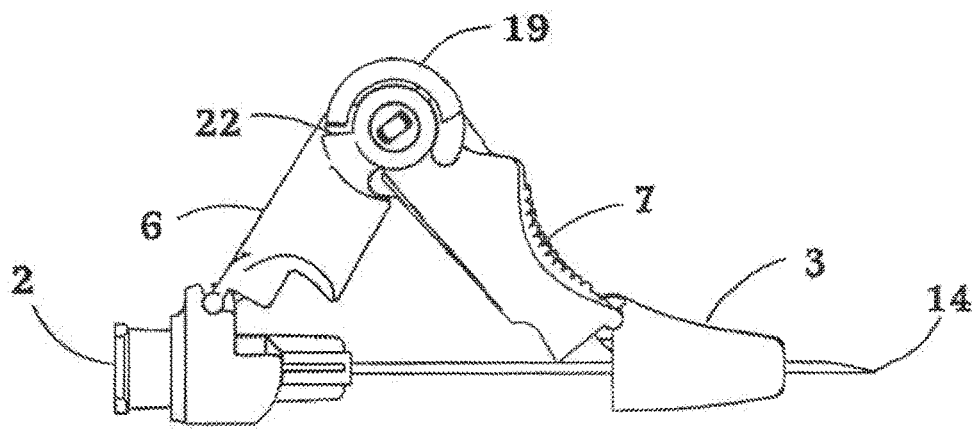
FIG. 22 is a side view of the device with a section through the latch disk cover exposing the wedge in its arrested position.

FIG. 22 is a side view of the device in its dislocated position with the resiliently biased latch disk (19) wedged up against the extended retention face (22) on the proximal cover segment (6).

Figures 23, 24:
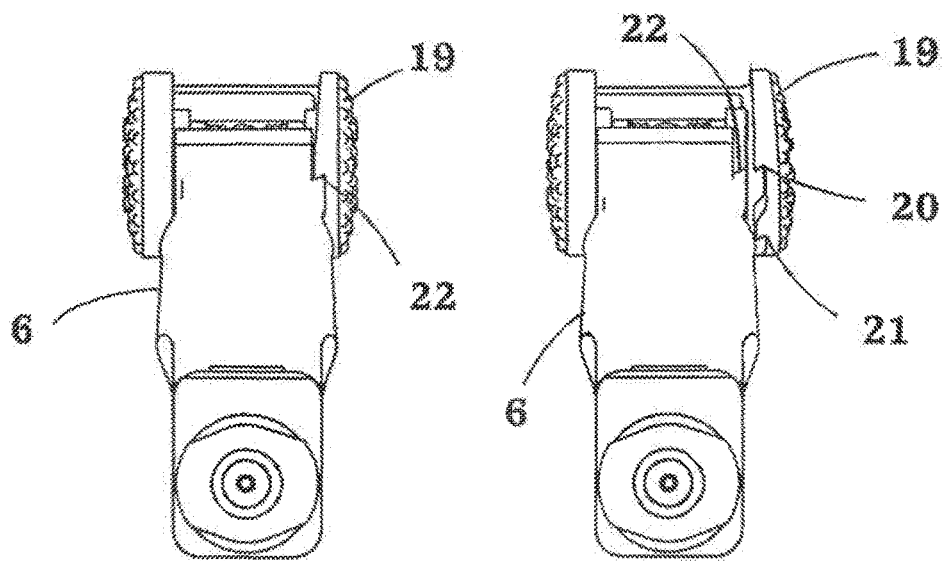
FIG. 23 is a rear view of the device showing the latch disk in its arrested position.
FIG. 24 is a rear view of the device showing the latch disk dislocated by a digital force applied to the distal end cap.

FIG. 23 is a rear view of the device in its dislocated position again showing the resiliently biased latch disk (19) wedged up against the extended retention face (22) on the proximal cover segment (6).

FIG. 24 is a rear view of the device with the resiliently biased latch disk (19) in its escaped position after the introduction of an external digital force.

Figure 25:
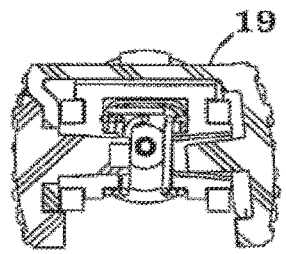
FIG. 25 is a sectioned view through the centre hinge showing the latch disk in its dislocated position.

FIG. 25 is a cross sectioned view of the resiliently biased latch disk (19) in its escaped position.

Figure 26:
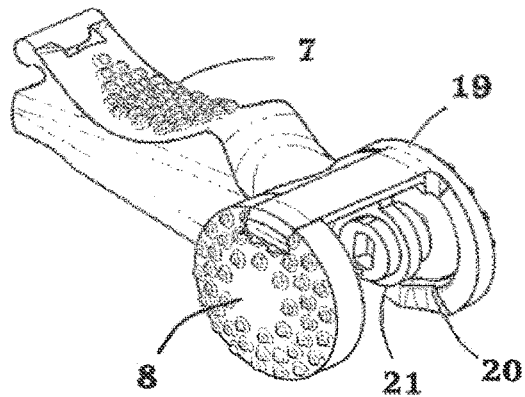
FIG. 26 is an isometric view of the distal cover segment with the latch disk secured in place by the retention disk.

FIG. 26 is an isometric view of the distal cover segment (7) with the resiliently biased Latch disk (19) mounted on it. The latch disk (19) has multiple recess features (20, 21) on its inside face that allows it to wedge into/against the proximal cover segment's said retention face extension when digitally activated. The multiple features add convenience for the user to selectively choose how far they need the needle (14) to extend past said distal end cap (3).

Figure 27:
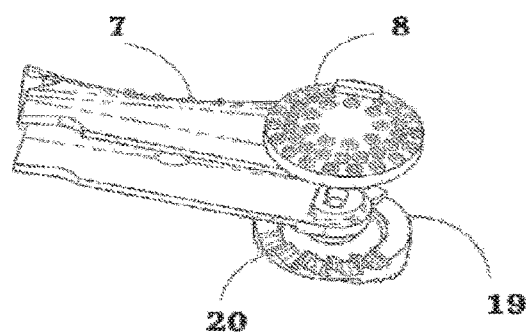
FIG. 27 is an bottom isometric view of the distal cover segment and latch disk showing the multiple recess features (20, 21) on its inside face.

FIG. 27 is an bottom isometric view of the distal cover segment and latch disk showing the multiple recess features (20, 21) on its inside face.

Figure 28:
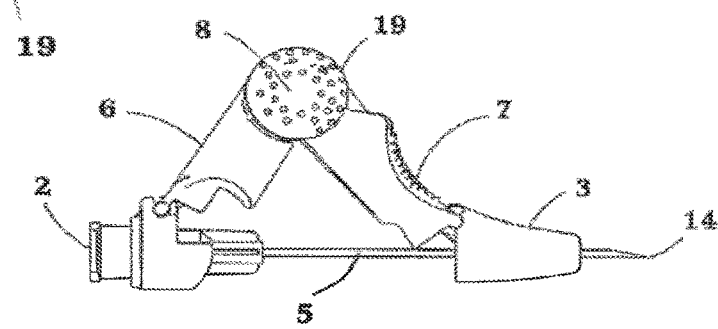
FIG. 28 is a side view of the device in its first temporally recessed and arrested position exposing the tip of the needle canulla.

FIG. 28 is a side view of the dislocated device at its first recessed feature (20 in FIG. 16) thereby exposing a small portion of the needle cannula (5 in earlier Figures).

Figure 29:
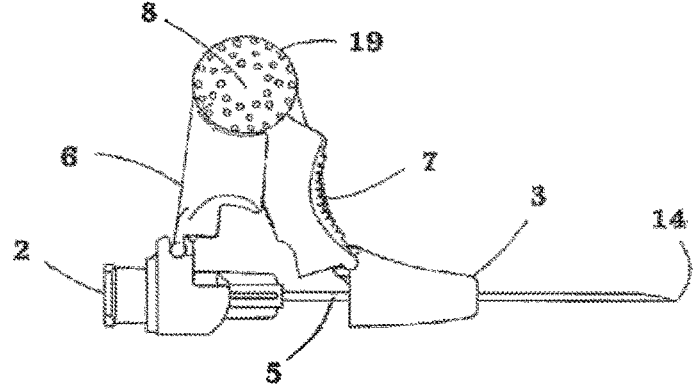
FIG. 29 is a side view of the device in its second temporally recessed and arrested position exposing a longer portion of the needle canulla.

FIG. 29 is a side view of the dislocated device at its second recessed feature (21 in FIG. 16) thereby exposing a longer section of the needle tip (14) from the cannula (5 in earlier Figures).

Figure 30:
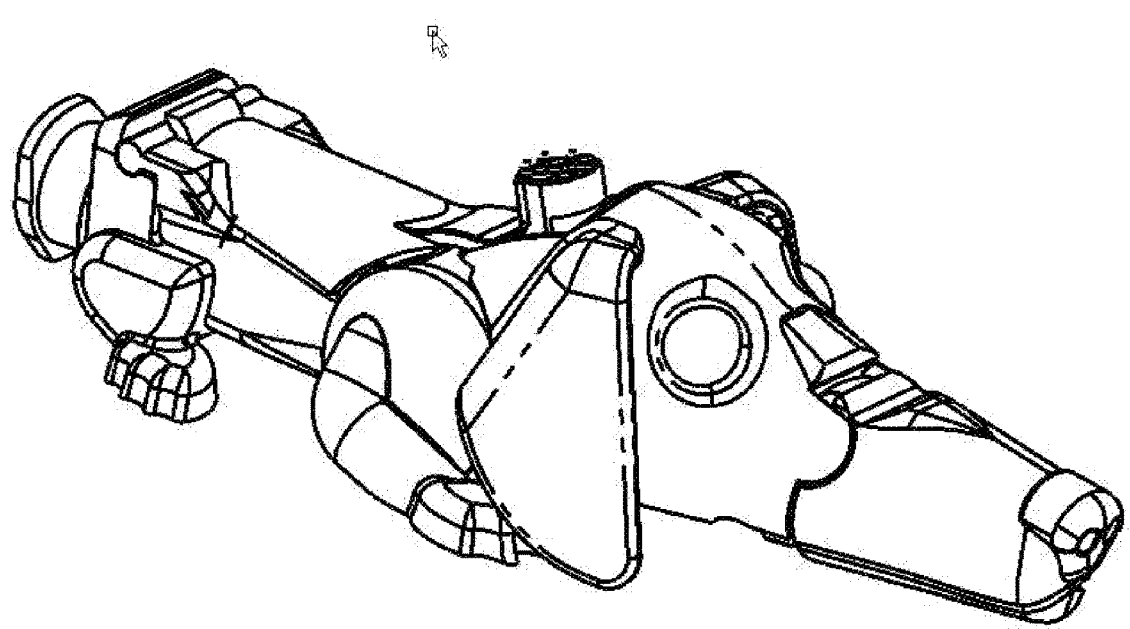
FIG. 30 is an isometric view of the device with the cover segments and end cap configured in the shape of an animal to act as a child friendly object
Figure 31:
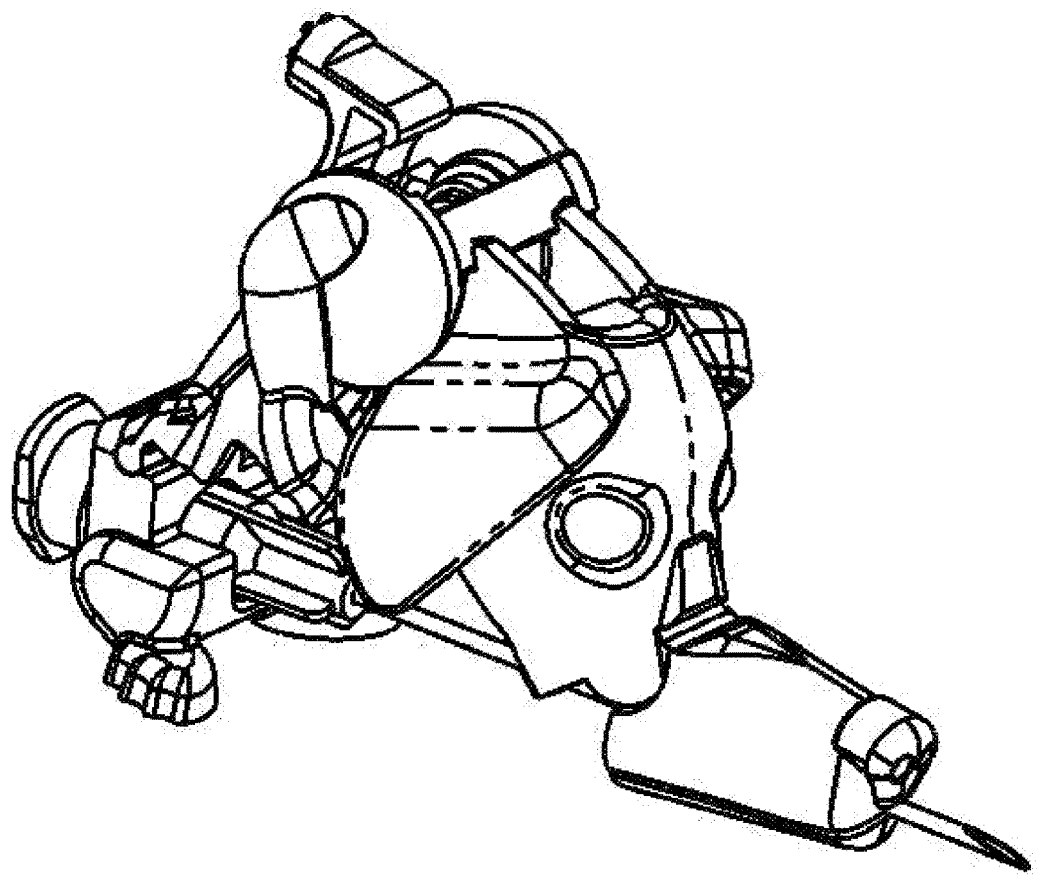
FIG. 31 is an isometric view of the child friendly configuration with the needle tip exposed just prior to fluid delivery

FIG. 30 is an isometric view of the device with the cover segments and end cap configured in the shape of an animal to act as a child friendly object FIG. 31 is an isometric view of the child friendly configuration with the needle tip exposed just prior to fluid delivery The above descriptions enable practice of the generic scope of the claims. It is to be noted that specific shapes, materials and relative dimensions in the disclosure may be altered to implement the device in varying medical fields without altering the underlying nature and performance of the invention.

What is claimed:

1. A segmented safety cover comprising: a) a proximal segment combined with a needle hub; b) a needle cannula that extends from the proximal needle hub to a distal sharpened end; c) a distal end cap with a hollow bore through which the needle cannula passes; d) a centrally mounted toggle locking mechanism, separating the proximal needle hub from the distal end cap, hingedly connected to both and maintaining the segmented safety cover in a position where it completely covers a needle tip on a needle; e) wherein the toggle locking mechanism is resistively bias-assisted and comprises a proximal cover segment and a distal cover segment which overlay the needle cannula and is linked together through a central hinge; f) said proximal cover segment and said distal cover segment of said toggle locking mechanism being configured with abutting faces that contact each other above said central hinge when the segmented safety cover is in a safety mode; g) wherein the proximal cover segment is connected to the hub via a proximal hinge and the distal cover segment is connected to the end cap via a distal hinge; and h) wherein the proximal hinge, abutting faces and distal hinge are in line and the central hinge is below the abutting faces in the safety mode so that a force exerted on the distal end cap is translated onto the abutting faces above the central hinge thereby maintaining the device in a secured state wherein the segmented safety cover is in a position where it completely covers the needle tip, while maintaining the distal end cap's position covering the needle tip extending through the needle cannula.

2. The segmented safety cover of claim 1 wherein the needle is present within the cover, and the segmented safety cover is configured so that the pointed injection end of the needle is completely covered by the distal end cap when the torsion spring is secured in the safety mode, and the pointed injection end of the needle is exposed from the distal end cap when the safety mode is removed and compressive force has been applied by the torsion spring, retracting the distal end cap by rotation of both the proximal cover segment and the distal cover segment about the central hinge.

3. The segmented safety cover of claim 1 wherein the proximal hinge, distal hinge and central hinge are configured to form a triangular configuration when the segmented safety cover is in a delivery mode for the needle within the needle cannula, and the distal cover segment and the distal end cap are configured to slide with respect to the needle cannula within the hollow bore, and wherein the abutting faces rotate away from each other, as the central hinge is elevated with top portions of the abutting faces having rotated with the central hinge farther away from each other than do lower portions of the abutting faces, when a force parallel to a plane formed between the abutting faces is applied upwardly towards the abutting faces.

4. The segmented safety cap of claim 3 wherein upon forming the triangular configuration, the distal end cap is configured to retract over the needle cannula and towards the needle hub, and relative to the distal cover, appears to rotate away from the distal cover segment and expose the injection end of the needle.

5. The segmented safety cover of claim 3 wherein the torsion spring comprises a double coil spring with a first extension of the double coil spring extending approximately parallel to the distal segment in the safety mode, and a second extension of the double coil spring extending approximately parallel to the proximal segment in the safety mode.

6. The segmented safety cover of claim 3 wherein in the safety mode, the distal cover segment and proximal cover segment are in the secured state, resisting movement of the distal cover segment and the proximal cover segment by the torsion spring.

7. The segmented safety cover of claim 6 wherein two manually operated pressure plates that overlap sides of the distal cover segment and the proximal cover segment are configured to dislocate the secured state when pressure is applied to the two pressure plates to apply a dislocating force vector approximately parallel to the two abutting faces and cause the two abutting faces to rotate away from each other to end the safety mode.

8. The segmented safety cover of claim 7 where said pressure plates are resiliently biased to disengage from a dislocated mode to return to the secured state and a ready mode when triggered by said distal end cap when the distal end cap pushes against a patient's skin during the injection procedure, where said dislocated pressure plates release the segmented safety cover to return to its secured state as the needle is withdrawn from the patient.

9. The segmented safety cover of claim 1 wherein the torsion spring comprises a double coil spring with a first extension of the double coil spring extending approximately parallel to the distal segment in the safety mode, and a second extension of the double coil spring extending approximately parallel to the proximal segment in the safety mode.

10. A segmented safety cover comprising: a) a proximal segment combined with a needle hub; b) a needle cannula that extends from the proximal needle hub to a distal sharpened end; c) a distal end cap with a hollow bore through which the needle cannula passes; d) a centrally mounted toggle locking mechanism, separating the proximal needle hub from the distal end cap, hingedly connected to both and maintaining the segmented safety cover in a position where it completely covers a needle tip on a needle; e) wherein the toggle locking mechanism is resistively bias-assisted and comprises a proximal cover segment and a distal cover segment which overlay the needle cannula and is linked together through a central hinge; f) said proximal cover segment and said distal cover segment of said toggle locking mechanism being configured with abutting faces that contact each other above said central hinge when the segmented safety cover is in a safety mode; g) wherein the proximal cover segment is connected to the hub via a proximal hinge and the distal cover segment is connected to the end cap via a distal hinge; and h) wherein the proximal hinge, abutting faces and distal hinge are in line and the central hinge is below the abutting faces in the safety mode so that a force exerted on the distal end cap is translated onto the abutting faces above the central hinge thereby maintaining the device in a secured state wherein the segmented safety cover is in a position where it completely covers the needle tip, while maintaining the distal end cap's position covering the needle tip extending through the needle cannula, wherein the torsion spring comprises a double coil spring with a first extension of the double coil spring extending approximately parallel to the distal segment in the safety mode, and a second extension of the double coil spring extending approximately parallel to the proximal segment in the safety mode, wherein a first one coil of the double coil spring is on a first side of the cannula shaft and a second one coil of the double coil spring is on a second and opposite side of the cannula shaft with respect to the first coil.

11. A method for enabling injection of fluids using the segmented safety cover with a needle present within the cover of claim 3 comprising applying force to both the proximal cover segment and the distal cover segment from the torsion spring to elevate the central hinge and retract the distal end cap to slide over the needle cannula to expose the needle tip; wherein the proximal hinge, distal hinge and central hinge are arranged in the form of an inverted triangle formed by a line connecting said proximal and said distal hinges that lies parallel to the needle cannula and said central hinge defining a vertex of the inverted triangle below said proximal and distal hinges, and an exposure position for the needle tip is created only when the central hinge is elevated above the line connecting said proximal and said distal hinges from the position of the central hinge as the vertex of the inverted triangle.

12. A segmented safety cover comprising: a) a proximal segment fixed with a needle hub, said proximal segment also being integrated with a blood collecting needle; b) a distal end cap with a hollow bore that covers a needle tip on the blood collecting needle through which said needle cannula may pass; c) a rigidly interlocked, torsion spring assisted centrally hinged toggle locking mechanism that covers the needle cannula, where said center segment comprises a hollow proximal cover segment and distal hollow cover segment linked through a central hinge; d) wherein said proximal cover segment and distal cover segment are configured with two vertical, contacting and abutting faces above said central hinge; e) wherein a proximal cover segment of said central toggle locking mechanism is hingedly connected to said proximal segment by a proximal hinge and said distal cover segment of said central toggle locking mechanism is hingedly connected to said distal end cap by a distal hinge; f) wherein the proximal hinge, distal hinge and central hinge are arranged in the form of an inverted triangle formed by a line connecting said proximal and said distal hinges that lies parallel to the cannula shaft and said central hinge defining a vertex of the inverted triangle below said proximal and distal hinges; and g) wherein an exposure position for a needle from within the cannula shaft is created only when the central hinge is elevated above the line connecting said proximal and said distal hinges from the position of the central hinge as the vertex of the inverted triangle; wherein, when the two vertical abutting faces are in a safety mode abutting each other, a vector force passing through the central hinge towards the abutting faces, the vector forces causes the central hinge to elevate and rotate and the abutting faces to rotate away from each other.

13. The segmented safety cover according to claim 12 wherein said central toggle locking mechanism includes a resiliently biased wedge mechanism which is configured to be pressure activated to arrest said toggle locking mechanism in a temporary dislocated position to enable exposure of said cannula tip prior to the invasive procedure.

14. The segmented safety cover according to claim 13 wherein said wedge mechanism comprises a resiliently biased wedge extension mounted on the distal cover segment or proximal cover segment, and the spring-loaded wedge is located above the center hinge.

15. The segmented safety cap of claim 14 wherein said wedge is configured to be clamped into a wedged-in position by spring force generated by the torsion spring, and wherein the wedge is configured to be resiliently biased to disengage from a wedged-in position when pressure applied by the torsion spring is reduced when said distal end cap pushes against a patient's skin.

16. The segmented safety cover of claim 15 where said torsion spring is centred to and fitted on an inside of said centre hinge and comprises single or double coil loops on one or either side of the needle that allows the center hinge to be lowered past said needle cannula without interference by said needle cannula.

17. The segmented safety cap of claim 15 wherein said resiliently biased wedge is integrated into a latch disk with single or multiple recess features on an inside face of the latch disk and a locking face on the wedge that allows it to wedge into or against a locking face on the proximal cover segment or distal cover segment when the wedge is pressure activated.

* * * * *